(12) United States Patent
Fariabi (10) Patent No.: US 6,827,734 B2
(45) Date of Patent: Dec. 7, 2004

(54) HIGH STRENGTH MEMBER FOR INTRACORPOREAL USE

(75) Inventor: Sepehr Fariabi, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 10/154,474

(22) Filed: May 23, 2002

(65) Prior Publication Data

US 2002/0147494 A1 Oct. 10, 2002

Related U.S. Application Data

(63) Continuation of application No. 09/071,680, filed on May 1, 1998, now Pat. No. 6,419,693, which is a division of application No. 08/829,465, filed on Mar. 28, 1997, now Pat. No. 6,482,166, which is a continuation of application No. 08/280,209, filed on Jul. 25, 1994, now Pat. No. 5,636,641.

(51) Int. Cl.$^7$ ................................................. A61F 2/06
(52) U.S. Cl. ...................................... 623/1.18; 623/1.15
(58) Field of Search ............................... 623/1.15, 1.16, 623/1.17–1.22

(56) References Cited

U.S. PATENT DOCUMENTS

| | | |
|---|---|---|
| 3,679,812 A | 7/1972 | Owens |
| 4,112,952 A | 9/1978 | Thomas et al. |
| 4,300,244 A | 11/1981 | Bokros |

(List continued on next page.)

FOREIGN PATENT DOCUMENTS

| | | |
|---|---|---|
| EP | 0 395 098 A1 | 10/1990 |
| EP | 0 480 427 A1 | 4/1992 |
| EP | 0 804 934 A2 | 11/1997 |
| WO | WO 96/25969 A2 | 8/1996 |
| WO | WO 98/02084 A2 | 1/1998 |
| WO | WO 98/33443 A1 | 8/1998 |
| WO | WO 99/16382 A2 | 4/1999 |
| WO | WO 99/44542 A2 | 9/1999 |

OTHER PUBLICATIONS

Application Ser. No. 08/164,986.
Application Ser. No. 09/054,320.
Application Ser. No. 10/449,499.
Letter from Food and Drug Administration re Magic WALL-STENT® Encoprothesis, Sept. 29, 1998.
Heat Treattment of Steel, (from the 1924 edition of Machinery's Handbook), downloaded from http://www.zianet.com/ebear/metal/heattreat3.html.
Standard Specification for Wrought Cobalt–20 Chromium–15 Tungsten–10 Nickel Alloy for Surgical Implant Applications (*UNS R30605*), ASTM Designation: F 90–97.
U.S. Ser. No. 07/647,464.
U.S. Ser. No. 08/149,985 filed Nov. 10, 1993.
U.S. Ser. No. 08/164,968.

*Primary Examiner*—Corrine McDermott
*Assistant Examiner*—Hieu Phan
(74) *Attorney, Agent, or Firm*—Fulwider Patton Lee & Utecht, LLP (57) ABSTRACT

This invention is directed to an intracorporeal device formed of a high strength Co—Ni—Cr alloy and is particularly suitable for forming a composite product with a pseudoelastic member formed of NiTi alloy. Suitable intracorporeal products include guidewires and stents. The high strength alloy consists essentially of about 28 to about 65% cobalt, about 2 to about 40% nickel, about 5 to about 35% chromium, up to about 12% molybdenum, up to about 20% tungsten, up to about 20% iron and the balance inconsequential amounts of impurities and other alloying constituents, with a preferred alloy composition including about 30 to about 45% cobalt, about 25 to about 37% nickel, about 15 to about 25% chromium and about 5 to about 15% molybdenum. Intravascular devices such as guidewires, stents and the like can be formed of this high strength Co—Ni—Cr alloy.

39 Claims, 4 Drawing Sheets

U.S. PATENT DOCUMENTS

| | | | |
|---|---|---|---|
| 4,452,908 A | 6/1984 | Ball et al. | |
| 4,516,972 A | 5/1985 | Samson | |
| 4,538,622 A | 9/1985 | Samson et al. | |
| 4,554,929 A | 11/1985 | Samson et al. | |
| 4,582,181 A | 4/1986 | Samson | |
| 4,655,771 A | 4/1987 | Wallsten | |
| 4,723,549 A | 2/1988 | Wholey et al. | |
| 4,830,003 A | 5/1989 | Wolff et al. | |
| 4,856,516 A | 8/1989 | Hillstead | |
| 4,917,104 A | 4/1990 | Rebell | |
| 4,922,927 A | 5/1990 | Fine et al. | |
| 4,925,445 A | 5/1990 | Sakamoto et al. | |
| 4,994,071 A | 2/1991 | MacGregor | |
| 4,997,435 A | 3/1991 | Demeter | |
| 5,019,090 A | 5/1991 | Pinchuk | |
| 5,061,275 A | 10/1991 | Wallsten et al. | |
| 5,064,435 A | 11/1991 | Porter | |
| 5,069,226 A | 12/1991 | Yamauchi et al. | |
| 5,100,425 A | 3/1992 | Fischell et al. | |
| 5,135,503 A | 8/1992 | Abrams | |
| 5,171,383 A | 12/1992 | Sagaye et al. | |
| 5,195,984 A | 3/1993 | Schatz | |
| 5,197,978 A | 3/1993 | Hess | |
| 5,203,348 A | 4/1993 | Dahl et al. | |
| 5,213,111 A | 5/1993 | Cook et al. | |
| 5,217,483 A | 6/1993 | Tower | |
| 5,230,348 A | 7/1993 | Ishibe et al. | |
| 5,238,004 A | 8/1993 | Sahatjian et al. | |
| 5,242,451 A | 9/1993 | Harada et al. | |
| 5,258,020 A | 11/1993 | Froix | |
| 5,267,564 A | 12/1993 | Barcel et al. | |
| 5,282,845 A | 2/1994 | Bush et al. | |
| 5,303,704 A | 4/1994 | Molacek et al. | |
| 5,333,625 A | 8/1994 | Klien | |
| 5,341,818 A | 8/1994 | Abrams et al. | |
| 5,358,517 A | 10/1994 | Pohndorf et al. | |
| 5,358,818 A | 10/1994 | Wilson et al. | |
| 5,421,955 A | 6/1995 | Lau et al. | |
| 5,449,372 A | 9/1995 | Schmaltz et al. | |
| 5,449,373 A | 9/1995 | Pinchasik et al. | |
| 5,465,733 A | 11/1995 | Hinohara et al. | |
| 5,477,864 A | 12/1995 | Davidson | |
| 5,496,359 A * | 3/1996 | Davidson | 607/115 |
| 5,512,291 A | 4/1996 | Li | |
| 5,514,154 A * | 5/1996 | Lau et al. | 623/1.15 |
| 5,562,729 A | 10/1996 | Purdy et al. | |
| 5,569,295 A | 10/1996 | Lam | |
| 5,607,467 A | 3/1997 | Froix | |
| 5,628,787 A | 5/1997 | Mayer | |
| 5,636,641 A | 6/1997 | Fariabi | |
| 5,679,470 A | 10/1997 | Mayer | |
| 5,713,917 A | 2/1998 | Leonhardt et al. | |
| 5,720,300 A | 2/1998 | Fagan et al. | |
| 5,824,077 A * | 10/1998 | Mayer | 623/11.11 |
| 5,846,251 A | 12/1998 | Hart | |
| 5,876,432 A | 3/1999 | Lau et al. | |
| 5,882,329 A | 3/1999 | Patterson et al. | |
| 5,891,191 A | 4/1999 | Stinson | |
| 5,891,193 A * | 4/1999 | Robinson et al. | 128/898 |
| 6,017,362 A | 1/2000 | Lau | |
| 6,066,158 A | 5/2000 | Engelson et al. | |
| 6,419,693 B1 * | 7/2002 | Fariabi | 623/1.18 |
| 6,482,166 B1 | 11/2002 | Fariabi | |

* cited by examiner

HIGH STRENGTH MEMBER FOR INTRACORPOREAL USE

RELATED APPLICATIONS

This is a continuation application of application having U.S. Ser. No. 09/071,680, filed May 1, 1998 now U.S. Pat. No. 6,419,693; which is divisional of U.S. Ser. No. 08/829,465, filed Mar. 28, 1997 now U.S. Pat. No. 6,482,166; which is a continuation of U.S. Ser. No. 08/280,209, filed on Jul. 25, 1994 now U.S. Pat. No. 5,636,641; all of whose contents are hereby incorporated by reference.

BACKGROUND OF THE INVENTION

This invention relates to the field of intracorporeal medical devices, and more particularly to elongated intravascular members such as guidewires for percutaneous transluminal coronary angioplasty (PTCA) and stents for maintaining body lumen patency after the body lumen has been dilated with a balloon.

In PTCA procedures a guiding catheter is percutaneously introduced into the cardiovascular system of a patient in a conventional Seldiger technique and advanced therein until the distal tip of the guiding catheter is seated in the ostium of a desired coronary artery. A guidewire is positioned within an inner lumen of a dilatation catheter and then both the catheter and guidewire are advanced through the guiding catheter to the distal end thereof. The guidewire is first advanced out of the distal end of the guiding catheter into the patient's coronary vasculature until the distal end of the guidewire crosses a lesion to be dilated, then the dilatation catheter having an inflatable balloon on the distal portion thereof is advanced into the patient's coronary anatomy over the previously introduced guidewire until the balloon is properly positioned across the lesion. Once in position across the lesion, the balloon is inflated one or more times to a predetermined size with radiopaque liquid to dilate the stenosis. The balloon is then deflated so that blood flow will resume through the dilated artery and the dilatation catheter and the guidewire can be removed therefrom.

Conventional guidewires for angioplasty and other vascular procedures usually comprise an elongated core member with one or more tapered sections near its distal end and a flexible body such as a helical coil disposed about a distal portion of the core member. A shapable member, which may be the distal extremity of the core member or a separate shaping ribbon such as described in U.S. Pat. No. 5,135,503, hereby incorporated into this application by reference, extends through the flexible body and is secured to a rounded plug at the distal end of the flexible body. Torquing means are provided on the proximal end of the core member to rotate, and thereby steer, the guidewire while it is being advanced through a patient's vascular system. The core member is typically formed of stainless steel, although core member formed of pseudoelastic NiTi alloys are described in the literature and have been used to a limited extent in clinical applications.

Further details of guidewires, and devices associated therewith for angioplasty procedures can be found in U.S. Pat. No. 4,516,972 (Samson); U.S. Pat. No. 4,538,622 (Samson et al.); U.S. Pat. No. 4,554,929 (Samson et al.); and copending application Ser. No. 07/994,679 (Abrams et al.) which are incorporated into this application by reference.

Steerable dilatation catheters with fixed, built-in guidewires or guiding members, such as described in U.S. Pat. No. 4,582,181 (now Re 33,166) are frequently used because they have better pushability than over-the-wire dilatation catheters where the guidewires are slidably disposed within the guidewire lumens of the catheters.

A major requirement for guidewires and other guiding members is that they have sufficient column strength to be pushed through a patient's vascular system or other body lumen without kinking. However, they must also be flexible enough to avoid damaging the blood vessel or other body lumen through which they are advanced. Efforts have been made to improve both the strength and flexibility of guidewires in order to make them more suitable for their intended uses, but these two properties can be diametrically opposed to one another in that an increase in one usually involves a decrease in the other. Efforts to combine a separate relatively stiff proximal section with a relatively flexible distal section frequently result in an abrupt transition at the junction of the proximal and distal section due to material differences.

What has been needed and heretofore unavailable is an elongated intravascular body, such as a guidewire, a stent or the like, which exhibits much higher strength coupled with good ductility than materials currently used to form these types of intravascular devices.

SUMMARY OF THE INVENTION

The present invention is directed to a high strength alloy containing cobalt, nickel, and chromium and particularly to a composite product having a portion formed of the high strength cobalt-nickel-chromium alloy and a portion formed of pseudoelastic alloy such as NiTi alloy.

The product of one embodiment of the invention is an elongated member configured for advancement within a body lumen and is formed at least in part, of high strength alloy comprising about 28 to about 65% cobalt, about 2 to about 40% nickel, about 5 to about 35% chromium and up to about 12% molybdenum. Other alloying components include up to about 20% tungsten, up to about 20% iron and up to about 3% manganese. The alloy may also contain inconsequential amounts of other alloying constituents, as well as impurities, typically less than 0.5% each. A presently preferred alloy composition for use in the intracorporeal product consists essentially of about 30 to about 45% cobalt, about 25 to about 37% nickel, about 15 to about 25% chromium and about 5 to about 15% molybdenum. As used herein all references to percent composition are weight percent unless otherwise noted. The high strength alloy has ultimate strengths up to and exceeding 300 ksi.

Preferably, the intracorporeal product is formed by first cold working the high strength alloy at least 40% of its original transverse cross-sectional area in a plurality of cold working stages with the cold worked product being intermediate annealed between cold working stages at a temperature between about 600° and 1200° C. Those alloys containing molydenum are age hardenable after cold working and annealing at a temperature between about 400° and about 700° C. For optimum tensile strength properties the aging is conducted at about 550° to about 680° C., particularly when the high strength alloy is combined with other alloys as described hereinafter.

In another embodiment of the invention, the cobalt-nickel-chromium alloy is formed into a composite structure with a NiTi alloy which contains about 25 to about 47% titanium and the balance nickel and up to 10% of one or more additional alloying elements. Such other alloying elements may be selected from the group consisting of up to 3% each of iron, cobalt, platinum, palladium and chromium and up to about 10% copper and vanadium. This alloy preferably has a stable austenite phase at body temperature (about 37° C.) and exhibits pseudoelasticity with a stressed induced transformation of the austenite phase to a martensite phase at body temperature at a stress level well above about 50 ksi, preferably above 70 ksi and in many cases above about 90 ksi. The stress levels causing the complete stress-induced transformation of the austenite phase to the martensite phase results in a strain in the specimen of at least about 4%, preferably over 5%. The region of phase transformation resulting from stress preferably begins when the specimen has been strained about 1 to 2% at the onset of the phase change from austenite to martensite and extends to about 7 to about 9% strain at the completion of the phase change. The stress and strain referred to herein is measured by tensile testing. Other methods for determining the stress-strain relationship, e.g., applying a bending moment to a cantilevered specimen, provide a different relationship from the relationship determined by tensile testing, because the stresses which occur in the specimen during bending are not as uniform as they are in tensile testing. The rate of change in stress during the phase transformation is considerably less than the rate of change thereof either before or after the stress-induced transformation. The stress level is relatively constant within the transformation period.

To form the elongated pseudoelastic NiTi member, the alloy material is first cold worked in a plurality of stages, preferably by drawing, to effect a size reduction of at least about 30% and up to about 70% or more in the original transverse cross section thereof with intermediate annealing between the cold working stages at temperatures between about 600° to about 800° C. for about 5 to about 30 minutes. After the final cold working stage the cold worked product is given a final anneal at a temperature of about 700° C. to generate final properties. Preferably, the cold worked NiTi alloy product is subjected to tension during the final annealing and/or provided with a mechanical straightening followed by thermal treatment to help develop a straight memory. The ultimate tensile strength of the material is well above 200 ksi with an ultimate elongation at failure of about 15%.

In one aspect of the invention the cobalt-nickel-chromium containing alloy and another alloy such as the NiTi alloy described above are cold worked together into a composite product, with both alloys being subjected to the same thermomechanical processing to develop a desirable combination of properties. In particular, a presently preferred thermomechanical processing includes a plurality of drawing steps with a reduction of at least about 25% in each cold working stage. The cold worked product is intermediate annealed between cold working stages at a temperature of about 600° and 900° C., e.g. about 750° C. with a time at temperature of about 10 to about 15 minutes. The amount of cold work in the last working stage should be at least about 50% and can be as high as 95% or more. However, the actual cold working in the final working stage is usually determined by the elongation or ductility desired in the final product after straightening and aging.

In the above embodiment the elongated Ni—Ti alloy product is an inner member disposed within the inner lumen of an elongated sheath formed of a Co—Ni—Cr—Mo alloy with an appropriate lubricant and then the assembled unit is processed in a series of size reduction steps involving drawing, or other cold working, followed by an intermediate annealing as described above. The annealing may be performed in line with the drawing. The Co—Ni—Cr—Mo alloy sheath and the NiTi alloy inner member should be recrystallization annealed prior to assembly and cold work to provide maximum ductility by maintaining an equiaxed grain structure and minimum grain growth. After the final cold working step, the composite product is heat treated at a temperature between about 500° and 700° C. and preferably between about 550° and 675° C. for about one minute to about four hours to age harden the cladding and provide pseudoelastic characteristics to the inner member. Tension may be applied during the aging treatment to straighten the product while it is being aged and to provide a straight memory to the NiTi alloy portion of the composite. For composite products with an inner member formed of alloys other than Ni—Ti alloys, the aging conditions, i.e. the temperature and the time at temperature, may be different than that described above for NiTi alloys.

In an alternative embodiment, the NiTi alloy product and the Co—Ni—Cr alloy product can be first prepared separately to their desired final properties and then combined together by suitable means to form the composite product. For example, after final processing, the Co—Ni—Cr alloy sheath can be heated to expand the inner lumen therein so that an NiTi inner member can be readily inserted therein. After insertion of the NiTi inner member into the inner lumen of the sheath, the latter can be cooled so that it shrink fits about the NiTi inner member. Alternatively, the NiTi inner member can be inserted into the sheath after processing while the sheath is still at elevated temperatures and then cooled to contract the sheath onto the NiTi inner member. Other means for combining the NiTi product and the Co—Ni—Cr product includes the use of an adhesive bond therebetween or a physical connection such as a set screw extending through the sheath into the core member or some other type of mechanical connection. A wide variety of other means for joining the Ni—Ti product and the Co—Ni—Cr are contemplated and will become apparent to those skilled in the art.

The products of the invention exhibit a very high level of tensile strength, yet they have excellent ductility. The age hardened Co—Ni—Cr—Mo alloy can have ultimate tensile strengths above 300 ksi and the NiTi alloys can have ultimate tensile strengths exceeding 200 ksi. These products are biocompatible and are particularly useful in medical devices, which are to be utilized intracorporeally, such as guidewires, stents and the like.

One embodiment of the present invention is directed to an expandable stent which is relatively flexible along its longitudinal axis to facilitate delivery through tortuous body lumens, but which is stiff and stable enough radially in an expanded condition to maintain the patency of a body lumen such as an artery when implanted therein.

The stent of the invention generally includes a plurality of radially expandable cylindrical elements which are relatively independent in their ability to expand and to flex relative to one another. The individual radially expandable cylindrical elements of the stent are dimensioned so as to be longitudinally shorter than their own diameters. Interconnecting elements or struts extending between adjacent cylindrical elements provide increased stability and are preferably positioned to prevent warping of the stent upon the expansion thereof. The resulting stent structure is a series of radially expandable cylindrical elements which are spaced longitudinally close enough so that small dissections in the wall of a body lumen may be pressed back into position against the lumenal wall, but not so close as to compromise the longitudinal flexibility of the stent. The individual cylindrical elements may rotate slightly relative to adjacent cylindrical elements without significant deformation, cumulatively giving a stent which is flexible along its length and about its longitudinal axis but which is still very stiff in the radial direction in order to resist collapse.

The stent embodying features of the invention can be readily delivered to the desired lumenal location by mounting it on an expandable member of a delivery catheter, for example a balloon, and passing the catheter-stent assembly through the body lumen to the implantation site. A variety of means for securing the stent to the expandable member on the catheter for delivery to the desired location are available. It is presently preferred to compress the stent onto the balloon. Other means to secure the stent to the balloon include providing ridges or collars on the inflatable member to restrain lateral movement, or using bioresorbable temporary adhesives.

The presently preferred structure for the expandable cylindrical elements which form the stents of the present invention generally have a circumferential undulating pattern, e.g. serpentine. The transverse cross-section of the undulating component of the cylindrical element is relatively small and preferably has an apect ratio of about two to one to about 0.5 to one (e.g., the ratio of the height to the width of an undulation). A one to one apect ratio has been found particularly suitable. The open reticulated structure of the stent allows for the perfusion of blood over a large portion of the arterial wall which can improve the healing and repair of a damaged arterial lining.

The radial expansion of the expandable cylinder deforms the undulating pattern thereof similar to changes in a waveform which result from decreasing the waveform's amplitude and the frequency. Preferably, the undulating patterns of the individual cylindrical structures are in phase with each other in order to prevent the contraction of the stent along its length when it is expanded. The cylindrical structures of the stent are plastically deformed when expanded (except with NiTi alloys) so that the stent will remain in the expanded condition and, therefore, they must be sufficiently rigid when expanded to prevent the collapse thereof in use. With superelastic NiTi alloys, the expansion occurs when the stress of compression is removed so as to allow the phase transformation from austenite back to martensite and as a result the expansion of the stent.

The elongated elements or members which interconnect adjacent cylindrical elements should have a transverse cross-section similar to the transverse dimensions of the undulating components of the expandable cylindrical elements. The interconnecting elements may be formed in a unitary structure with the expandable cylindrical elements from the same intermediate product, such as a tubular element, or they may be formed independently and connected by suitable means, such as by welding or by mechanically securing the ends of the interconnecting elements to the ends of the expandable cylindrical elements. Preferably, all of the interconnecting elements of a stent are joined at either the peaks or the valleys of the undulating structure of the cylindrical elements which form the stent. In this manner there is no shortening of the stent upon expansion, when measured from the outermost ends of the interconnecting members connected to the cylindrical elements at opposite ends of the stent.

The number and location of elements interconnecting adjacent cylindrical elements can be varied in order to develop the desired longitudinal flexibility in the stent structure both in the unexpanded as well as the expanded condition. These properties are important to minimize alteration of the natural physiology of the body lumen into which the stent is implanted and to maintain the compliance of the body lumen which is internally supported by the stent. Generally, the greater the longitudinal flexibility of the stent, the easier and the more safely it can be delivered to the implantation site.

In a presently preferred embodiment of the invention the stent is conveniently and easily formed by coating stainless steel hypotubing with a material resistant to chemical etching, and then removing portions of the coating to expose portions of underlying tubing which are to be removed to develop the desired stent structure. The exposed portions of the tubing are removed by chemically etching from the tubing exterior leaving the coated portion of the tubing material in the desired pattern of the stent structure. The etching process develops smooth openings in the tubing wall without burrs or other artifacts which are characteristic of mechanical or laser machining processes in the small sized products contemplated. Moreover, a computer controlled laser patterning process to remove the chemical resistive coating makes photolithography technology adaptable to the manufacture of these small products. The forming of a mask in the extremely small sizes needed to make the small stents of the invention would be a most difficult task. A plurality of stents can be formed from one length of hypotubing by repeating the stent pattern and providing small webs or tabs to interconnect the stents. After the etching process, the stents can be separated by severing the small webs or tabs which connect them. The stents may further be electrochemically polished in an aqueous solution and treated, if desired by applying a biocompatible coating.

These and other advantages of the invention will become more apparent from the following detailed description of the invention when taken in conjunction with the accompanying exemplary drawings.

DETAILED DESCRIPTION OF THE INVENTION

Figure 1:
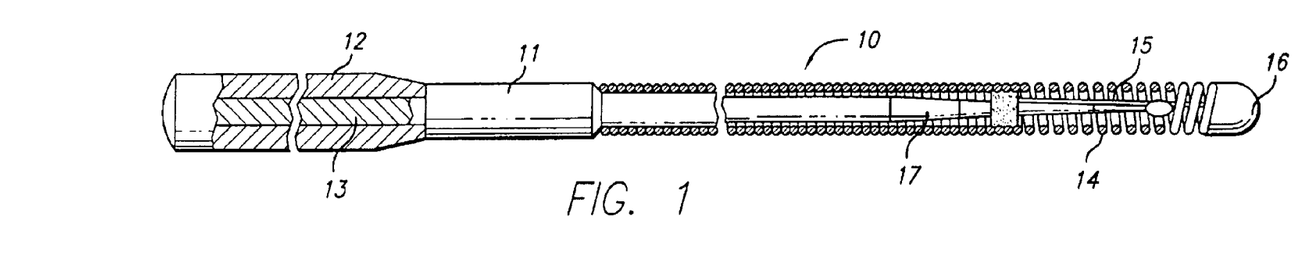
FIG. 1 is an elevational view, partially in section, of a guidewire embodying features of the invention.

FIG. 1 illustrates a guidewire 10 which includes a core member 11 having an outer sheath 12 formed of a Co—Ni—Cr alloy and an inner member 13 formed of Ni—Ti, a helical coil 14 on the distal end of the core member with a shaping ribbon 15 extending between the distal end of the core member and a rounded plug 16 which connects the distal end of the shaping ribbon with the distal end of the helical coil. The distal section 17 of the core member 11, which is disposed primarily within the coil 14, is tapered to sequentially smaller diameters to provide gradually increasing flexibility along the length of the distal portion of the guidewire 10. The taper is formed by removing the sheath 12 formed of high strength Co—Ni—Cr alloy which exposes the inner NiTi alloy member 13 having moderate strength and substantial flexibility which may then be ground in a conventional manner to one or more smaller diameter sections.

Figure 2:
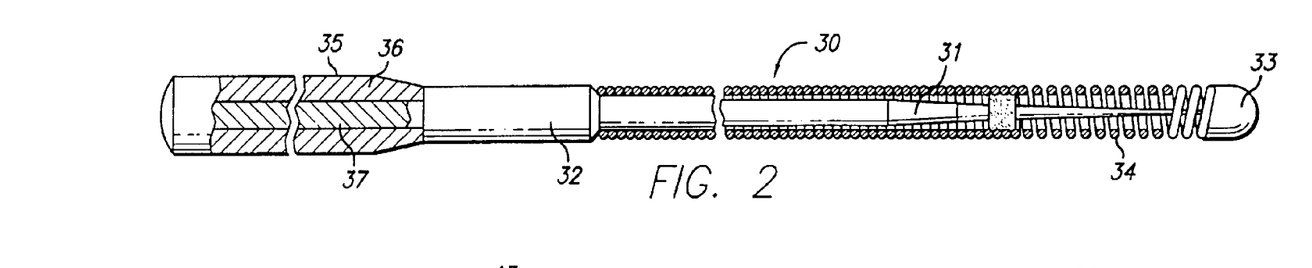
FIG. 2 is an elevational view, partially in section, of an alternative guidewire structure embodying features of the invention.

FIG. 2 depicts a guidewire 30 with a construction wherein the tapered distal section 31 of the core member 32 extends to the plug 33 which connects the distal end of the core member to the distal end of the helical coil 34 disposed about the distal section of the core member. The proximal section 35 of the core member 32 is of composite construction as in the prior embodiment with a sheath 36 of high strength Co—Ni—Cr alloy and an inner member 37 of a pseudoelastic NiTi alloy. The high strength sheath 36 is removed from the core member to form the tapered distal section 31 to increase the flexibility of the distal section of the guidewire 30.

The elongated proximal portions of the guidewires are generally about 130 to about 140 cm in length with an outer diameter of about 0.006 to about 0.018 inch for coronary use. Larger diameter guidewires may be employed in peripheral arteries and other body lumens. The lengths of the smaller diameter and tapered sections can range from about 2 to about 20 cm, depending upon the stiffness or flexibility desired in the final product. The helical coil is about 20 to about 45 cm in length, has an outer diameter about the same size as the diameter of the elongated proximal portion, and is made from wire about 0.002 to about 0.003 inch in diameter. The shaping ribbon and the flattened distal section of distal portion have rectangular transverse cross-sections which usually have dimensions of about 0.001 by 0.003 inch. The overall length of a guidewire is typically about 175 cm.

A presently preferred cobalt-nickel containing alloy is commercially available as MP35N from Carpenter Technology Corporation which has a nominal composition of about 35% cobalt, about 35% nickel, about 20% chromium and about 10% molybdenum. Other commercially available alloys include Elgiloy from Elgiloy Limited Partnership and Haynes 188 from Haynes International.

The following example is given to illustrate the method of forming the core member of a guidewire in accordance with the invention. A NiTi alloy rod having a composition of about 55.9% Ni and 44.1% Ti was drawn to a diameter of about 0.06 inch. The as-drawn wire, which was in a cold worked condition (e.g. 50% cold work), was ground or etched to remove tenaceous surface oxides and then annealed at 700° C. for about one hour. A tubular sheath having a nominal composition of 35% Co, 35% Ni, 20% Cr and 10% Mo was formed with an outer diameter of about 0.114 inch and an inner diameter of about 0.068 inch in an annealed condition. The NiTi wire was disposed within the inner lumen of the high strength sheath and the assembly was drawn in a series of five stages with a 50% reduction in area followed by heat treating at 750° C. for 15 minutes in each stage. The fifth stage was followed by a sixth stage which included drawing with a cold work of about 16% followed by heat treating at 750° C. and a seventh stage which included drawing with a cold work of about 50% but with no heat treating. The final cold worked product was aged at temperatures of about 650° for about one minute to develop maximum bending, yield and modulus with minimum spring back.

The composite core member of the invention provides a number of favorable properties and characteristics. The outer sheath of high strength cobalt-nickel alloy provides the necessary stiffness and push and the inner NiTi alloy member provides the desirable distal flexibility. Another advantage of the composite product of the present invention, when utilized as a core member of a guidewire, is that the proximal end of the flexible coil can be soldered or brazed to the Co—Ni—Cr alloy sheath so as to avoid the problems with soldering the coil to a NiTi alloy which is very difficult to bond to by conventional soldering techniques because of the tenaceous oxide which usually forms on the surfaces of titanium containing alloys.

Figure 3:
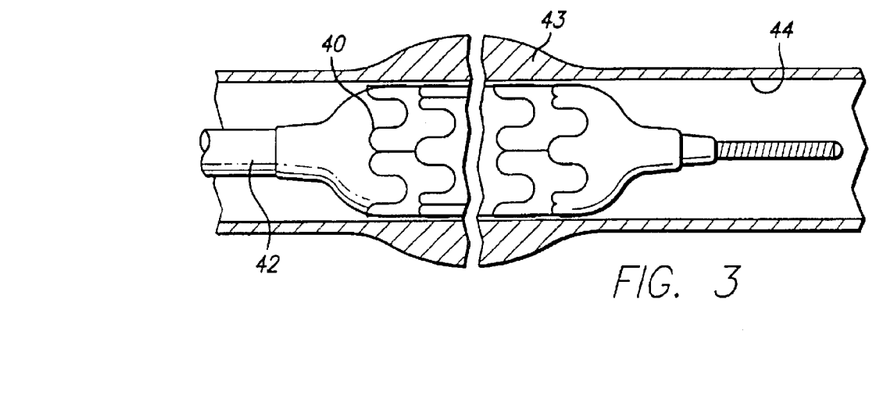
FIG. 3 is an elevational view, partially in section of a stent being expanded by an inflatable balloon on an intravascular catheter within a stenosed region of a patient's artery.
Figure 4:
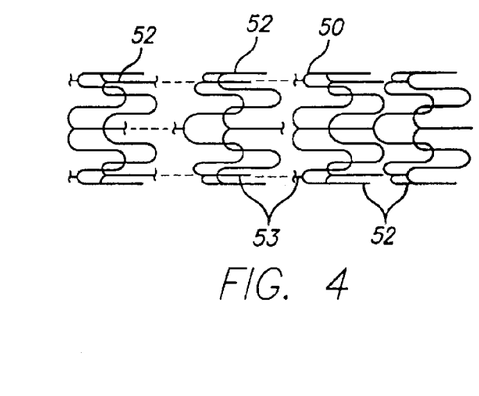
FIG. 4 is a perspective view of an intravascular stent which may be formed of the alloy composition of the invention.

FIGS. 3 and 4 illustrate another embodiment of the invention wherein the high strength Co—Ni—Cr alloy is in the form of an intraluminal stent 40, which as shown in FIG. 3, is expanded by the balloon 41 of catheter 42 within a stenosis 43. After permanent expansion of the stent 40 within the body lumen 44, such as a coronary artery, the balloon 41 is deflated and the catheter 42 withdrawn. The high strength developed by the Co—Ni—Cr alloy allows the stent to be formed of thinner material, yet provide the radial rigidity to hold the body lumen upon deflation of the balloon. The balloon utilized to expand the stent is similar in many respects to a dilatation balloon used in angioplasty procedures in that it is a generally inelastic balloon formed of a suitable polymeric material such as a high density polyethylene, polyethylene terephthalate and polyolefin, e.g. Surlyn®. A particularly suitable stent design is disclosed in copending application Ser. No. 08/164,986, filed on Dec. 9, 1993 which is assigned to the present assignee and which is incorporated herein by reference.

FIG. 4 is an enlarged perspective view of the stent 50 shown in FIGS. 3 and 5–7 with one end of the stent shown in an exploded view to illustrate in greater detail the placement of interconnecting elements 53 between adjacent radially expandable cylindrical elements 52. Each pair of the interconnecting elements 53 on one side of a cylindrical element 52 are preferably placed to achieve maximum flexibility for a stent. In the embodiment shown in FIG. 8 the stent 50 has three interconnecting elements 53 between adjacent radially expandable cylindrical elements 52 which are 120 degrees apart. Each pair of interconnecting elements 53 on one end of a cylindrical element 52 are offset radially 60 degrees from the pair on the other side of the cylindrical element. The alternation of the interconnecting elements results in a stent which is longitudinally flexible in essentially all directions. Various configurations for the placement of interconnecting elements are possible, and several examples are illustrated schematically in FIGS. 9–12. However, as previously mentioned, all of the interconnecting elements of an individual stent should be secured to either the peaks or valleys of the undulating structural elements in order to prevent shortening of the stent during the expansion thereof.

Figure 5:
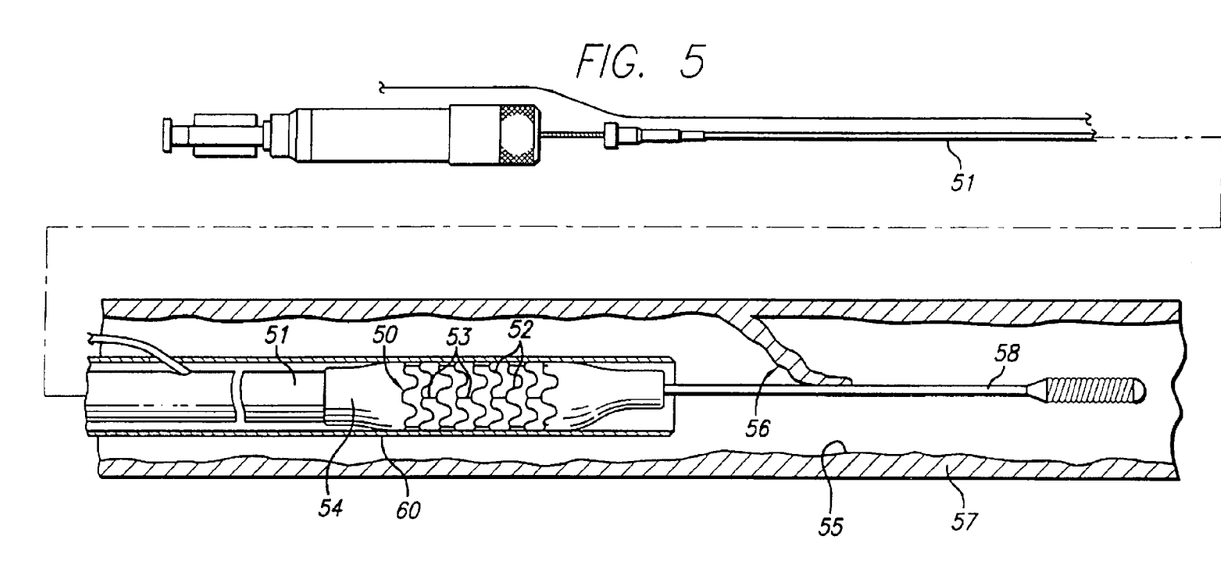
FIG. 5 is an elevational view, partially in section, of a stent embodying features of the invention which is mounted on a delivery catheter and disposed within a damaged artery.

FIG. 5 illustrates a stent 50 incorporating features of the invention which is mounted onto a delivery catheter 51. The stent generally comprises a plurality of radially expandable cylindrical elements 52 disposed generally coaxially and interconnected by elements 53 disposed between adjacent cylindrical elements. The delivery catheter 51 has an expandable portion or balloon 54 for expanding of the stent 50 within an artery 55. The artery 55, as shown in FIG. 5, has a dissected lining 56 which has occluded a portion of the arterial passageway.

The delivery catheter 51 onto which the stent 50 is mounted, is essentially the same as a conventional balloon dilatation catheter used for angioplasty procedures. The balloon 54 may be formed of suitable materials such as polyethylene, polyethylene terephthalate, polyvinyl chloride, nylon and ionomers such as Surlyn® manufactured by the Polymer Products Division of the Du Pont Company. Other polymers may also be used. In order for the stent 50 to remain in place on the balloon 54 during delivery to the site of the damage within the artery 55, the stent 50 is compressed onto the balloon. A retractable protective delivery sleeve 20 as described in co-pending application Ser. No. 07/647,464, filed on Apr. 25, 1990 and entitled STENT DELIVERY SYSTEM may be provided to further ensure that the stent stays in place on the expandable portion of the delivery catheter 51 and prevent abrasion of the body lumen by the open surface of the stent 50 during delivery to the desired arterial location. Other means for securing the stent 50 onto the balloon 54 may also be used, such as providing collars or ridges on the ends of the working portion, i.e., the cylindrical portion, of the balloon.

Each radially expandable cylindrical element 52 of the stent 50 may be independently expanded. Therefore, the balloon 54 may be provided with an inflated shape other than cylindrical, e.g. tapered, to facilitate implantation of the stent 50 in a variety of body lumen shapes.

In a preferred embodiment, the delivery of the stent 50 is accomplished in the following manner. The stent 50 is first mounted onto the inflatable balloon 54 on the distal extremity of the delivery catheter 51. The balloon 54 is slightly inflated to secure the stent 50 onto the exterior of the balloon. The catheter-stent assembly is introduced within the patient's vasculature in a conventional Seldinger technique through a guiding catheter (not shown). A guidewire 58 is disposed across the damaged arterial section with the detached or dissected lining 56 and then the catheter-stent assembly is advanced over a guidewire 58 within the artery 55 until the stent 50 is directly under the detached lining 56. The balloon 54 of the catheter is expanded, expanding the stent 50 against the artery 55, which is illustrated in FIG. 2. While not shown in the drawing, the artery 55 is preferably expanded slightly by the expansion of the stent 50 to seat or otherwise fix the stent 50 to prevent movement. In some circumstances during the treatment of stenotic portions of an artery, the artery may have to be expanded considerably in order to facilitate passage of blood or other fluid therethrough.

Figure 6:
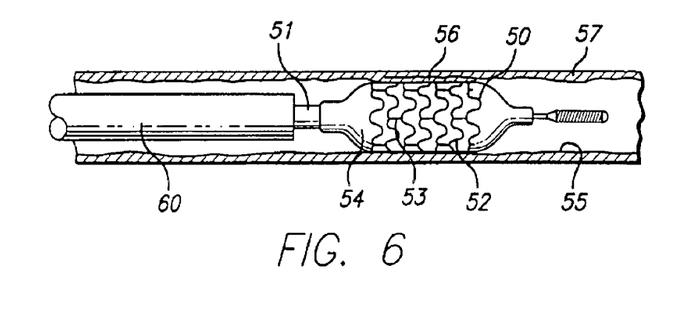
FIG. 6 is an elevational view, partially in section, similar to that shown in FIG. 1 wherein the stent is expanded within as damaged artery, pressing the damaged lining against the arterial wall.
Figure 7:
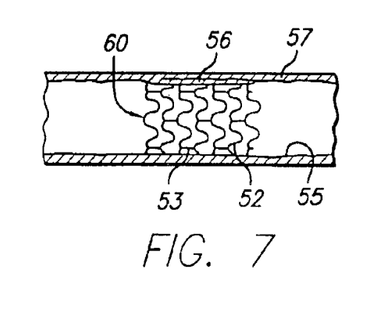
FIG. 7 is an elevational view, partially in section showing the expanded stent within the artery after withdrawal of the delivery catheter.

The stent 50 serves to hold open the artery 55 after the catheter 51 is withdrawn, as illustrated by FIG. 7. Due to the formation of the stent 50 from an elongated tubular member, the undulating component of the cylindrical elements of the stent 50 is relatively flat in transverse cross-section, so that when the stent is expanded, the cylindrical elements are pressed into the wall of the artery 55 and as a result do not interfere with the blood flow through the artery 55. The cylindrical elements 52 of stent 50 which are pressed into the wall of the artery 55 will eventually be covered with endothelial cell growth which further minimizes blood flow interference. The undulating portion of the cylindrical sections 52 provide good tacking characteristics to prevent stent movement within the artery. Furthermore, the closely spaced cylindrical elements 52 at regular intervals provide uniform support for the wall of the artery 55, and consequently are well adapted to tack up and hold in place small flaps or dissections in the wall of the artery 55 as illustrated in FIGS. 6 and 7.

Figure 12:
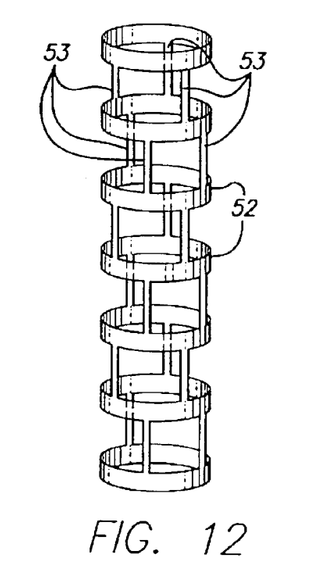

FIG. 12 illustrates a stent of the present invention wherein three interconnecting elements 53 are disposed between radially expandable cylindrical elements 52. The interconnecting elements 53 are distributed radially around the circumference of the stent at a 120 degree spacing. Disposing four or more interconnecting elements 53 between adjacent cylindrical elements 52 will generally give rise to the same considerations discussed above for two and three interconnecting elements.

Figure 13:
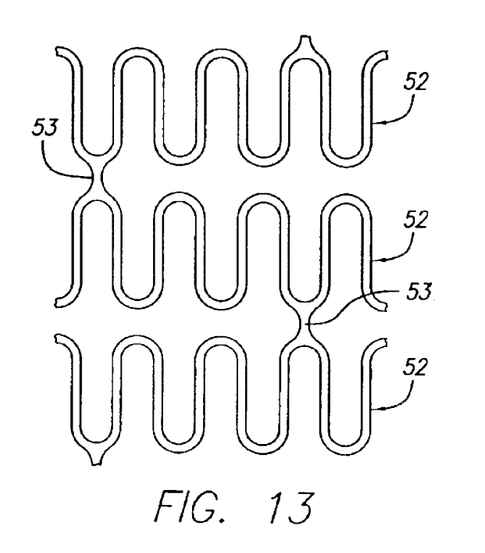
FIG. 13 is a plan view of a flattened section of a stent illustrating an alternate undulating pattern in the expandable cylindrical elements of the stent which are out of phase.

The properties of the stent 50 may also be varied by alteration of the undulating pattern of the cylindrical elements 53. FIG. 13 illustrates an alternative stent structure in which the cylindrical elements are in serpentine patterns but out of phase with adjacent cylindrical elements. The particular pattern and how many undulations per unit of length around the circumference of the cylindrical element 52, or the amplitude of the undulations, are chosen to fill particular mechanical requirements for the stent such as radial stiffness.

Figure 8:
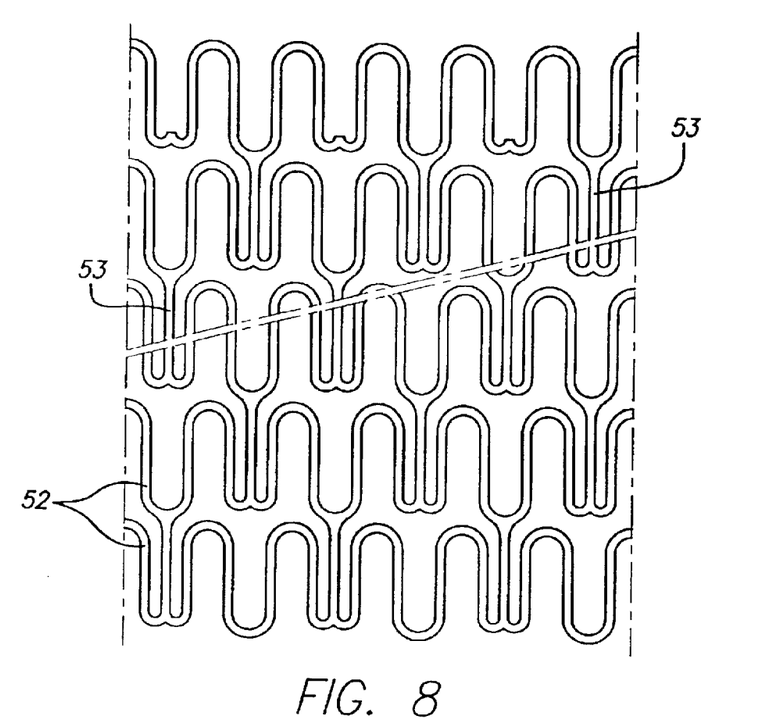
FIG. 8 is a plan view of a flattened section of a stent of the invention which illustrates the undulating pattern of the stent shown in FIG. 4.
Figure 9:
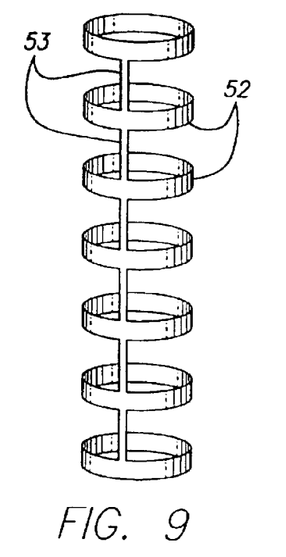
FIGS. 9 through 12 are perspective views schematically illustrating various configurations of interconnective element placement between the radially expandable cylindrical elements of the stent.
Figure 10:
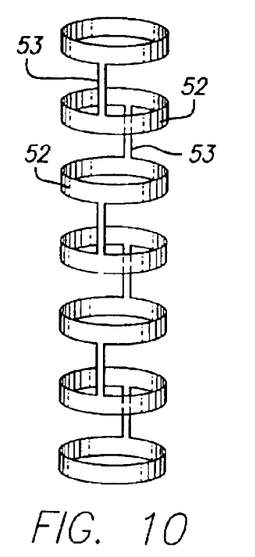
Figure 11:
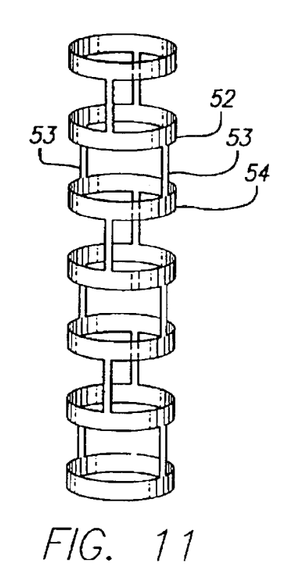

The number of undulations may also be varied to accommodate placement of interconnecting elements 53, e.g. at the peaks of the undulations or along the sides of the undulations as shown in FIGS. 8 and 13.

Figure 14:
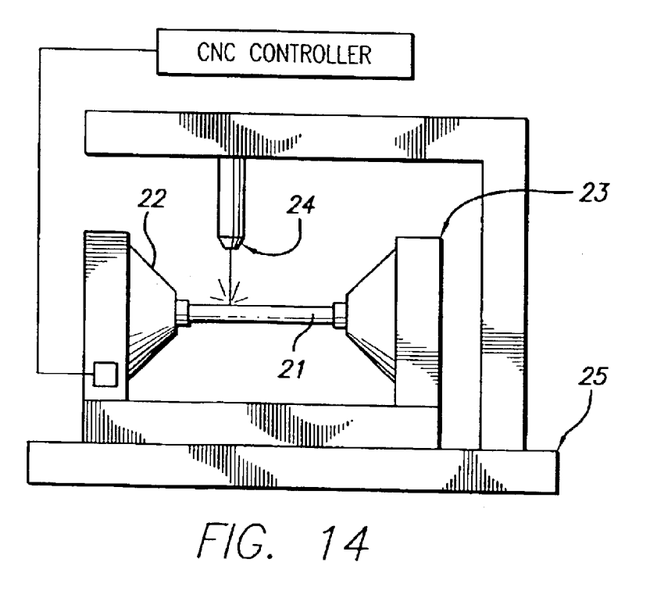
FIG. 14 is a schematic representation of equipment for selectively removing coating applied to tubing in the manufacturing of the stents of the present invention.

The stent 50 of the present invention can be made in many ways. However, the preferred method of making the stent is to coat a thin-walled tubular member, such as stainless steel hypotubing, with a material which is resistive to chemical etchants, and then to remove portions of the coating to expose the underlying hypotubing which is to be removed but to leave coated portions of the hypotubing in the desired pattern for the stent so that subsequent etching will remove the exposed portions of the metallic tubing, but will leave relatively untouched the portions of the metallic tubing which are to form the stent. The coated portion of the metallic tube is in the desired shape for the stent. An etching process avoids the necessity of removing burrs or slag inherent in conventional or laser machining processes. It is preferred to remove the etchant-resistive material by means of a machine-controlled laser as illustrated schematically in FIG. 14. The stent may be electrochemically polished in an aqueous solution and treated, if desired, by applying a biocompatible coating.

While the present invention has been described herein in terms of certain preferred embodiments, those skilled in the art will recognize that a variety of modifications and improvements can be made to the present invention without departing from the scope thereof.

What is claimed is:

1. A stent comprising a cylindrically shaped tubular member having a plurality of non-helical cylindrical elements joined integrally by interconnecting members and further having metallic undulating structural elements wherein the entire cross-section of each metallic undulating structural element is composed of an alloy including cobalt in a concentration of between about 28 to about 65 percent by weight, chromium in a concentration of between about 5 to about 35 percent by weight, and nickel in a concentration of about 2 to about 40 percent by weight; and the cylindrically shaped tubular member is configured to be plastically expanded by an expandable member to a desired self supporting diameter suitable to hold open a body lumen.

2. The stent of claim 1, wherein the alloy further comprises molybdenum in a concentration up to about 12 percent by weight.

3. The stent of claim 1, wherein the alloy further comprises tungsten in a concentration up to about 20 percent by weight, iron in a concentration up to about 20 percent by weight, and manganese in a concentration up to about 3 percent by weight.

4. The stent of claim 1, wherein the alloy further comprises molybdenum in a concentration up to about 12 percent by weight, tungsten in a concentration up to about 20 percent by weight, iron in a concentration up to about 20 percent by weight, and manganese in a concentration up to about 3 percent by weight.

5. The stent of claim 1, wherein the cylindrically shaped tubular member includes a cylindrical element shaped in a serpentine pattern.

6. The stent of claim 1, wherein the cylindrically shaped tubular member includes a plurality of cylindrical elements joined together by interconnecting elements.

7. The stent of claim 6, wherein there are at least three interconnecting elements between adjacent cylindrical elements.

8. The stent of claim 1, further comprising metallic undulating structural elements being plastically expandable in a blood vessel for deployment therein.

9. The stent of claim 8, wherein the tubular member has a reticulated tubular structure having bounded openings for blood perfusion.

10. The stent of claim 9, wherein the reticulated tubular structure has a continuum body made from tubing.

11. The stent of claim 10, wherein the tubular structure has electrochemically polished tubular internal and external surfaces.

12. A stent comprising a tubular member having a plurality of non-helical cylindrical elements joined integrally by interconnecting members and further having metallic undulating structural elements wherein the entire cross-section of the metallic undulating structural elements is composed of an alloy including cobalt in a concentration of between about 28 to about 65 percent by weight, chromium in a concentration of between about 5 to about 35 percent by weight, and nickel in a concentration of between about 2 to about 40 percent by weight.

13. The stent of claim 12, wherein the alloy further comprises iron in a concentration of less than about 20 percent by weight, and manganese in a concentration of less than about 3 percent by weight.

14. The stent of claim 13, wherein the alloy further comprises molybdenum in a concentration of less than about 12 percent by weight.

15. The stent of claim 14, wherein the alloy further comprises tungsten in a concentration of less than about 20 percent by weight.

16. The stent of claim 12, wherein the tubular member is balloon expandable.

17. The stent of claim 12, wherein the tubular member includes a plurality of cylindrical elements each having a serpentine pattern.

18. The stent of claim 17, wherein the serpentine pattern is in-phase with adjacent cylindrical elements.

19. The stent of claim 17, wherein the serpentine pattern is out of phase with adjacent cylindrical elements.

20. A stent comprising a plurality of radially expandable cylindrical elements composed of an alloy including cobalt in a concentration of between about 28 to about 65 percent by weight, chromium in a concentration of between about 5 to about 35 percent by weight, nickel in a concentration of about 2 to about 40 percent by weight, tungsten in a concentration of up to about 20 percent by weight, iron in a concentration of up to about 20 percent by weight, and manganese in a concentration of up to about 3 percent by weight.

21. The stent of claim 20, wherein the alloy further includes molybdenum in a concentration of up to about 12 percent by weight.

22. The stent of claim 20, wherein the cylindrical elements are dimensioned to be longitudinally shorter than their own diameters.

23. The stent of claim 22, further including interconnecting elements disposed between adjacent cylindrical elements, wherein there are three interconnecting elements between adjacent cylindrical elements.

24. A stent comprising:
a plurality of radially expandable cylindrical elements;
the cylindrical elements composed of an alloy including cobalt in a concentration of between about 28 to about 65 percent by weight, chromium in a concentration of between about 5 to about 35 percent by weight, and nickel in a concentration of about 2 to about 40 percent by weight;
the cylindrical elements having an undulating component with a relatively flat cross-section; and
the cylindrical elements configured to be plastically expanded by an expandable member to a desired self supporting diameter suitable to hold open a body lumen.

25. A stent comprising:
a plurality of radially expandable, non-helical cylindrical elements;
the cylindrical elements having metallic undulating structural elements wherein the entire cross-section of the metallic undulating structural elements is composed of an alloy including cobalt in a concentration of between about 28 to about 65 percent by weight, chromium in a concentration of between about 5 to about 35 percent by weight, and nickel in a concentration of about 2 to about 40 percent by weight;
the cylindrical elements configured to be plastically expanded by an expandable member to a desired self supporting diameter suitable to hold open a body lumen;
the cylindrical elements having an electrochemically polished metallic surface; and
the cylindrical elements having been cold worked and age hardened.

26. The stent of claim 25, wherein the cylindrical elements have an undulating component with a relatively flat cross-section.

27. The stent of claim 26, wherein at least one of the cylindrical elements is out of phase with at least another one of the cylindrical elements.

28. A stent comprising:
a plurality of radially expandable cylindrical elements;

the cylindrical elements composed of an alloy including cobalt in a concentration of between about 28 to about 65 percent by weight, the alloy further including chromium, nickel, and tungsten;

the cylindrical elements configured to be plastically expanded by an expandable member to a desired self supporting diameter suitable to hold open a body lumen.

29. The stent of claim 28, wherein the alloy includes tungsten in a concentration up to about 20 percent by weight.

30. The stent of claim 28, wherein the percent by weight of chromium is between about 5 to about 35 percent and the percent by weight of nickel is about 2 to about 40 percent.

31. The stent of claim 28, wherein the cylindrical elements have a electrochemically polished surface and a biocompatible coating on the electrochemically polished surface.

32. The stent of claim 28, wherein the cylindrical elements have an undulating component with a relatively flat cross-section.

33. The stent of claim 32, wherein at least one of the cylindrical elements is out of phase with at least another one of the cylindrical elements.

34. The stent of claim 32, wherein the cross-section of the undulating component of the cylindrical elements has an aspect ratio of about one to one.

35. The stent of claim 32, wherein the cross-section of the undulating component of the cylindrical elements has a height-to-width aspect ratio of about two-to-one.

36. The stent of claim 30, further comprising undulations being plastically expandable in a blood vessel for deployment therein.

37. The stent of claim 36, wherein the plurality of radially expandable cylindrical elements have a reticulated tubular structure having bounded openings for blood perfusion.

38. The stent of claim 37, wherein the reticulated tubular structure has a continuum body made from tubing.

39. The stent of claim 38, wherein the plurality of radially expandable cylindrical elements have electrochemically polished tubular internal and external surfaces.

* * * * *